US010532148B2

(12) United States Patent
Frostaa et al.

(10) Patent No.: US 10,532,148 B2
(45) Date of Patent: Jan. 14, 2020

(54) IRRIGATION SYSTEM CONTAINER

(71) Applicant: Coloplast A/S, Humlebaek (DK)

(72) Inventors: Isak Frostaa, Malmoe (SE); Hans Falleboe, Gentofte (DK); Richard Morgan Hickmott, Helsingoer (DK); Niels Hvid, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/512,082

(22) PCT Filed: Sep. 21, 2015

(86) PCT No.: PCT/DK2015/050286
§ 371 (c)(1),
(2) Date: Mar. 17, 2017

(87) PCT Pub. No.: WO2016/041565
PCT Pub. Date: Mar. 24, 2016

(65) Prior Publication Data
US 2017/0274135 A1 Sep. 28, 2017

(30) Foreign Application Priority Data
Sep. 19, 2014 (DK) .................. 2014 00535

(51) Int. Cl.
*A61M 3/02* (2006.01)
(52) U.S. Cl.
CPC ........ *A61M 3/0258* (2013.01); *A61M 3/0295* (2013.01); *A61M 2205/502* (2013.01); *A61M 2210/1067* (2013.01)

(58) Field of Classification Search
CPC .... A61M 3/0258; A61M 3/02; A61M 1/0011; A61M 2210/1067; A61M 3/0295; A61M 3/0266; A61M 3/0245; A61M 3/00; A61M 3/0208; A61M 3/0233; A61M 3/0254; A61M 3/0279; A61M 5/00; A61J 1/10; A61F 5/445; B65D 1/32; B65D 11/18; B65D 1/0292; B65D 1/323; B65D 1/326;
(Continued)

(56) References Cited

U.S. PATENT DOCUMENTS

| 1,352,306 A | 9/1920 | Mott |
| 1,484,621 A | 2/1924 | Bond et al. |
| 1,647,210 A | 11/1927 | Bryans |

(Continued)

FOREIGN PATENT DOCUMENTS

| CN | 2160402 Y | 4/1994 |
| DE | 355323 A | 6/1922 |

(Continued)

*Primary Examiner* — Kami A Bosworth
*Assistant Examiner* — Alexandra Lalonde
(74) *Attorney, Agent, or Firm* — Coloplast Corp., Coloplast A/S; Nick Baumann

(57) ABSTRACT

A system for anal irrigation is provided. The system includes a container, an anal probe, tubes and an electrical pump. The container has two configurations, a first collapsed configuration and a second expanded configuration. In the first configuration, a cavity for storing tubes and the anal probe is provided. In the second configuration, the container has a cavity for containing irrigation liquid. The pump and valves is stored in a cavity towards the bottom of the container.

15 Claims, 4 Drawing Sheets

(58) Field of Classification Search
CPC .... B65D 21/0231; B65D 21/086; B29C 53/08
See application file for complete search history.

(56) References Cited

U.S. PATENT DOCUMENTS

| | | | |
|---|---|---|---|
| 1,901,069 A | 3/1933 | Williams | |
| 2,253,571 A | 8/1941 | Miller | |
| 3,398,743 A | 8/1968 | Shalit | |
| 3,690,315 A | 9/1972 | Chittenden et al. | |
| 3,773,046 A | 11/1973 | Rosenberg | |
| 3,854,479 A * | 12/1974 | Duke | A61M 3/0245 206/229 |
| 3,888,235 A | 6/1975 | May et al. | |
| 4,014,322 A | 3/1977 | Shah | |
| 4,178,931 A * | 12/1979 | Lind | A61M 3/0258 137/355.16 |
| 4,828,546 A | 5/1989 | McNeil et al. | |
| 5,201,893 A | 4/1993 | Holloway et al. | |
| 5,292,242 A * | 3/1994 | Robbins, III | B29C 53/08 425/342.1 |
| 5,386,735 A | 2/1995 | Langdon | |
| 5,505,707 A | 4/1996 | Manzie et al. | |
| 6,264,636 B1 | 7/2001 | Holm et al. | |
| 6,391,010 B1 | 5/2002 | Wilcox | |
| 7,717,325 B2 | 5/2010 | Puls et al. | |
| 2003/0073963 A1 | 4/2003 | Falconer | |
| 2005/0215961 A1 | 9/2005 | Romano et al. | |
| 2006/0009732 A1 | 1/2006 | Hardy | |
| 2008/0275381 A1 * | 11/2008 | Mombrinie | A61M 3/0258 604/28 |
| 2010/0204681 A1 * | 8/2010 | Luther | A61M 3/0262 604/540 |
| 2014/0005602 A1 * | 1/2014 | Andreen | A61M 3/0258 604/98.02 |
| 2018/0043087 A1 * | 2/2018 | Foley | A61M 3/0295 |

FOREIGN PATENT DOCUMENTS

| | | | |
|---|---|---|---|
| EP | 3069744 A1 * | 9/2016 | ......... A61M 3/0233 |
| FR | 1222961 A | 6/1960 | |
| FR | 2307989 A1 | 11/1976 | |
| FR | 2750855 A1 | 1/1998 | |
| GB | 06031 A | 1/1912 | |
| GB | 19107 | 8/1913 | |
| GB | 137316 A | 3/1921 | |
| WO | 88/00840 A1 | 2/1988 | |
| WO | 94/14045 A1 | 6/1994 | |
| WO | 9838109 A1 | 9/1998 | |
| WO | 03/030969 A1 | 4/2003 | |
| WO | 03030968 A1 | 4/2003 | |
| WO | 04050534 A2 | 6/2004 | |
| WO | 2005/011776 A1 | 2/2005 | |

* cited by examiner

IRRIGATION SYSTEM CONTAINER

The invention relates to a container for anal irrigation purposes.

SUMMARY OF THE INVENTION

The invention relates to an anal irrigation system including a collapsible container. The container has two stable configurations, a first collapsed configuration and a second expanded configuration. In the collapsed configuration, the container provides room for the tubes and anal probe in a cavity that is present in the collapsed configuration. In the expanded configuration, the container provides room for irrigation liquid in a cavity that is present in the expanded configuration. A compact and easy to use system is thus obtained.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 illustrates the container in the first collapsed configuration, FIG. 3 illustrates the container in the second expanded configuration.

FIG. 7 illustrates the container in an expanded configuration. FIG. 8 illustrates the container in a collapsed configuration.

DETAILED DESCRIPTION OF THE INVENTION

Figure 1:
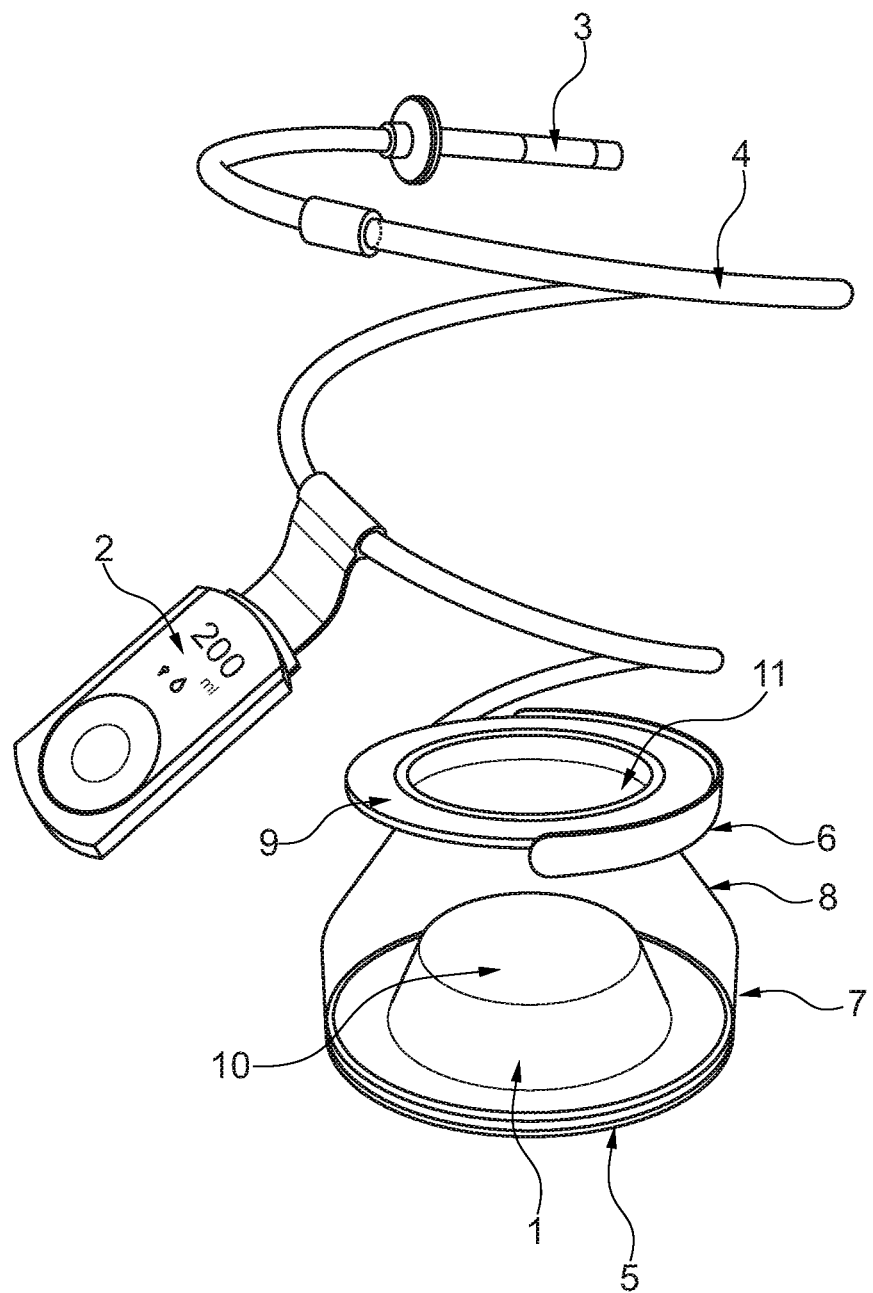
FIG. 1 illustrates a perspective view of an embodiment of an anal irrigation system with a collapsible container. The container is illustrated as partly transparent.

Anal irrigation is one of a number of treatments used to aid people with bowel problems. People suffering from bowel problems are often paralyzed, typically due to spinal cord injuries, and confined to a wheelchair or hospitalized. In these situations, often the peristaltic functions, i.e. the reflexes and muscles of the bowel, cannot be stimulated correctly. This results in constipation or random discharge of bowel contents. By using anal irrigation, a stimulation of the peristaltic movements of the colon can be provided. To perform such anal irrigation, a device comprising an anal probe, also called anal catheter, rectal catheter or speculum, is provided. The anal probe is inserted into the rectum through the anus. The anal probe is typically retained in the rectum by retention means, most commonly a balloon, which is inflated against the wall of the rectum. A liquid, such as water or a saline solution, is then introduced into the rectum through the anal probe. The amount of liquid is generally up to 1.5 litres, depending on the person.

Embodiments relate to an irrigation system comprising an anal probe, tubes, an electrical pump and a container having two configurations
 a first configuration where it is collapsed
 a second configuration where it is expanded,
the container having a first cavity for the pump and a second cavity in the collapsed position for the tubes and catheter, and the container further having a third cavity in the expanded configuration for containing irrigation liquid.

The effect of the invention is to provide a compact irrigation system that is easy to use. The second cavity defined in the collapsed configuration allows storing of the tubes and anal probe in a dry environment—that is outside of the cavity that holds the irrigation liquid, the third cavity. Thus, the tubes and anal probe will not be in contact with the third cavity during storage. The first cavity provides room for an electrical pump and valves inside the container.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the anal probe is to be inserted and the distal end is the opposite end—the end furthest away from the user when the anal probe is to be inserted.

The longitudinal direction is the direction from the distal to the proximal end. The transverse direction is the direction perpendicular to the longitudinal direction, which corresponds to the direction across the shaft of the anal probe.

By collapsible is meant that the container is able to fold onto itself in such a way that a part of the container is folded inside another part of the container. In other words, the container is collapsible in such a way that a part of the container is deformed into another configuration thus allowing the top part of the container to be positioned inside the bottom part of the container—without any parts sliding into each other.

An irrigation system typically comprises a reservoir or container for irrigation liquid, an anal probe and tubing connecting those two. The system described here also includes a pump for pumping the irrigation liquid into the intestines. This system includes a switching system for switching the pumping between pumping irrigation liquid into the intestines and inflating the retention means.

The anal probe comprises a main tubular part, typically called a shaft, extending from the distal end to the proximal end. The tip is positioned in the proximal end of the anal probe and is provided as a rounded closed end of the shaft. The anal probe may comprise a connector in the distal end and may, in an embodiment, comprise a flared end of the anal probe so that the diameter of the connector increases with respect to the tubular part.

Usually anal probes used for anal irrigation are approximately 10-20 mm in diameter. The anal probe will typically be provided with eyelets in the proximal end, the eyelets communicating with an irrigation channel inside the anal probe, so that irrigation liquid pumped into the anal probe in the distal end can exit the anal probe through the eyelets at the proximal end. The anal probe of this invention is provided with a retention element, e.g. in form of an inflatable balloon, for retaining the anal probe inside the rectum during the irrigation procedure. For the purpose of inflating the balloon, the anal probe is provided with an inflation channel inside the anal probe, the inflation channel extending from the distal end of the anal probe and terminating under the balloon.

In the following, whenever referring to the height of the container, reference is made to the dimension of the container from the bottom to the top of the container, when it is placed on a level surface. The longitudinal direction is defined as the direction from the bottom to the top of the container, and the transverse direction is defined as the direction perpendicular to the longitudinal direction—that is the direction generally parallel to the bottom of the container.

The first cavity of the container is always present. It is an enclosure in the container that is used for containing the pump and valves for the pumping system. The enclosure will typically be liquid tight, thus this enclosure may be made of a hard plastic material, for example Acrylonitrile butadiene styrene (ABS).

The second cavity of the container is present only in the first configuration. The second cavity is defined at the outer surface of the container as the container is collapsed. In other words, the second cavity is an outside trench 21 in the container, which is present only in the collapsed second configuration.

The third cavity of the container is present only in the second configuration. The third cavity is defined at the inner surface of the container, as the container is expanded. In other words, the third cavity is the inside cavity of the container in the expanded second configuration.

In a first configuration, the container is collapsed. In the collapsed configuration, the container is compact and the overall height of the container from the bottom to the top is reduced.

In the second configuration, the container is expanded. This means that the overall height of the container is larger in the second configuration than in the first configuration.

Moreover, in the second configuration, the inside surfaces of the container define the third cavity, thus allowing an amount of liquid to be contained in the third cavity. The amount of irrigation liquid containable in the container may be approximately 1.2 litres.

The container may consist of several parts. As an example, the container may consist of a bottom, a bottom part, a transitional part and a neck part. The bottom part may define a square cross-sectional area, a circular cross-sectional area or an n-sided cross-sectional area, where n is larger than four. The dimension across the bottom is defined as the largest dimension of the cross-sectional area, e.g. for a circular cross-sectional area, it will be the diameter, and for a square cross-sectional area it will be the length of the diagonal.

The bottom part may be generally cylindrical extending from the bottom of the container with upstanding walls in a first height in the longitudinal direction.

By generally cylindrical is meant a shape that has a circular cross-section, although a slightly ellipsoid cross-section may also be contemplated. By slightly ellipsoid cross-section is meant a cross-section where the minor axis of the ellipse is 90% or more of the length of the major axis of the ellipse. The upstanding walls of the cylinder are vertical within ±10 degrees.

The bottom part may also have a quadrangular cross-section, such as square or rectangular with upstanding walls extending from the bottom. The upstanding walls are vertical within ±10 degrees.

The transitional part may be tapered extending from the bottom part and extending a second height in the longitudinal direction, while reducing the cross-sectional area defined by the transitional part. The transitional part may be connected to the bottom part through a thinned part of the wall of the container functioning as a first hinge element.

The neck part may be generally cylindrical extending from the transitional part with upstanding walls in a third height in the longitudinal direction. The neck part may be connected to the transitional part through a thinned part of the wall of the container functioning as a second hinge element.

In an embodiment, the second cavity is defined between the transitional part and the neck part of the container in the first collapsed configuration.

Thus, when the user is not using the irrigation system, the tubes may be coiled around the neck part of the container and thus stored in the second cavity in the first collapsed configuration.

In an embodiment, the bottom part and the transitional part are at an angle to each other, the angle being around 30-45 degrees. The angle between the bottom part and the transitional part is defined as the angle between the two parts, when the container is in the collapsed position.

The angle between the transitional part and the neck may also be 30-45 degrees. This angle between the transitional part and the neck is also defined as the angle between the two parts, when the container is in the collapsed position.

These angles may allow for an easy transition between the first collapsed configuration, where the neck part and the transitional part is pushed into the container—into the third cavity—and the second expanded configuration, where the neck part and the transitional part extends upwards from the bottom part of the container. If the angles are below 30 degrees, it would be difficult to provide the transition between the first collapsed configuration and the second expanded configuration and if the angles are above 45 degrees, the transition would happen too easily, thus the configurations would be less stable.

In other words, by providing the angles between 30 and 45 degrees, a container that has two stable configurations, a collapsed and an expanded, is provided.

In an embodiment, a connection between the bottom part and the transitional part is defined by a first hinge element, and the transitional part is bi-stable so that it has a first configuration, where it is bulging outwards from the inner volume of the container, and a second configuration, where it is bulging inwards towards the inner volume of the container. Thus, in the first configuration, the container is in the expanded configuration, and in the second configuration of the transitional part, the container is in the collapsed configuration. Due to the transitional part bulging outwards, when the container is in the expanded configuration, this embodiment has the advantage of providing a larger volume in the third cavity than would be possible with other configurations.

In an embodiment, the lid of the container closes off the second cavity towards the top of the container, when the container is in the second configuration.

The bottom part and the transitional part are the flexible parts of the container. They may be made of a material like silicone, thermoplastic elastomeric material or thermoplastic polyurethane.

The thickness of the material for the bottom part and the transitional part may be between 0.5 and 2.5 mm. In an example, the transitional part may be around 1 mm thick, e.g. 0.8 mm, and the bottom part may be around 2 mm thick.

In the hinged region providing the transition between the transitional part and the bottom part, the material may be slightly thinned, so that it may be around 0.5 mm thick.

The transition from the first configuration to the second configuration may be made by popping out the container.

This thickness and the material provides the tapered transitional part with a function as a springy element. For this purpose, the Shore value of the material may be between 40 Shore A and 70 Shore A. The springy element of the tapered transitional part allows the user to expand the container simply by "shaking" the container—and the gravity will allow the bottom to pop out.

This is partly due to the fact that the pump and valves are positioned in the first cavity towards the bottom of the container. Thus, the bottom of the container is rather heavy. As an example, the pump and valves weigh around 800 grams.

In an embodiment of the invention, the opening into the container is rather large, e.g. 100 mm in diameter.

The large opening (100 mm) will allow a user to put his/her hand into the container to wipe the inside with a cloth.

In an embodiment, the inside bottom of the container is wedge-shaped, so that the thickness of the bottom increases from one side of the container transversely across the container to the other side.

The wedge-shaped bottom will guide the liquid remains to one side of the container—making it easier to wipe the container.

The container may be provided with an inner tube extending from the bottom of the container to the outside surface of the container at the necking part of the container.

Figure 6:
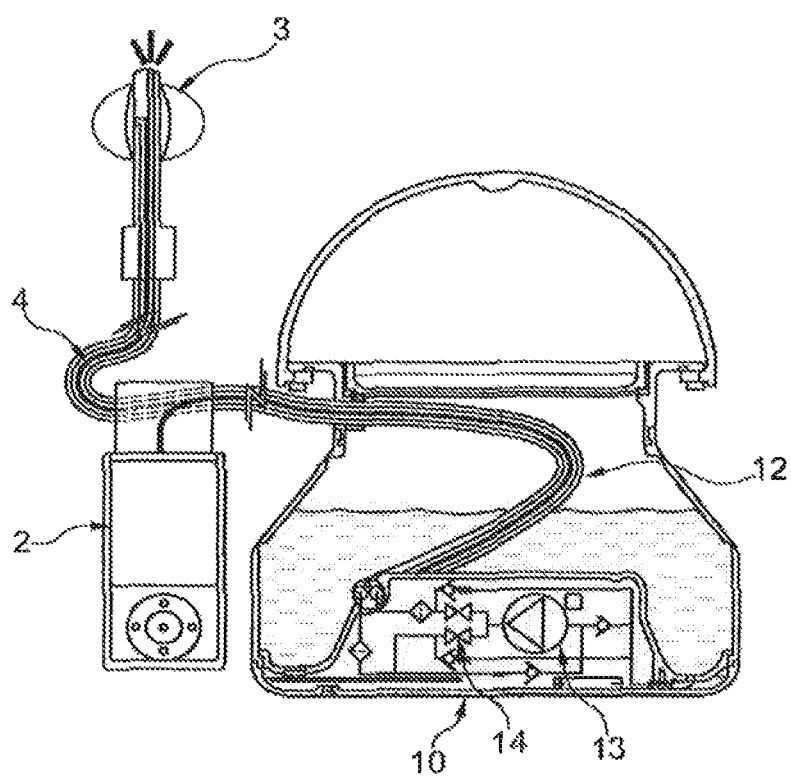
FIG. 6 illustrates an embodiment of an anal irrigation system with a collapsible container, the container is illustrated in a cross-sectional view, with a schematic outline of pumps and valves in the first cavity of the container.

The inner tube may have two parts. A first inner tube part extending from the bottom of the container to the pump in the first cavity and a second inner tube part extending from the pump to the neck part of the container for allowing connection to the outer tube. FIG. 6 shows an inner tube part 12 extending from the pump 13 located at the base of the container.

In an embodiment, the second inner tube part extends from the pump, through the top of the first cavity and curves slightly around the inside of the container to reach the neck part. At the neck part, the second inner tube part may be permanently attached to a through-going connecting piece for connecting the outer tubes to the outside of the neck part.

The neck part of the container may have an inner outline of a size allowing the first cavity to be received within the neck part in the collapsed configuration. As an example, the inner outline of the neck part is cylindrical with a diameter of 100 mm and the first cavity is cylindrical, or slightly cone-shaped, with a diameter of 80 mm.

In an embodiment, the dimension across the bottom is between 150 mm and 200 mm, for example 175 mm or around 165 mm. This dimension provides enough room outside of the first cavity to allow the desired amount of liquid (1.2 litres) to be contained in the third cavity. The dimensioning of the container is a compromise between reducing the dimension across the bottom and reducing the height in the collapsed configuration, while still allowing the transition between the collapsed configuration and the expanded configuration. If the dimension across the bottom is too small, then the height in the collapsed configuration would need to be larger—and thereby the container in the collapsed configuration will be un-handy and large. If the dimension across the bottom is too large, then the overall transverse dimension of the container will be too large—also in the collapsed configuration, where an overall small dimension of the container is desirable.

In an embodiment the height in the collapsed configuration is around 50 mm or even less, for example around 40 mm, whereas the height in the expanded configuration is around 100 mm or a little less, such as between 80 mm and 100 mm.

DETAILED DESCRIPTION OF THE DRAWING

Embodiments, and features of the various exemplary embodiments described in this application, may be combined with each other ("mixed and matched"), unless specifically noted otherwise.

FIG. 1 illustrates an embodiment of an irrigation system. The system includes a container 1, a control unit 2 and a probe 3. Furthermore, there is a tube 4 connecting the container 1 with the probe 3.

The container 1 is in FIG. 1 shown in the second expanded configuration. The container 1 has a bottom 5 and a top 6. The bottom part 7 of the container extends from the bottom and a first height towards the top. The transitional part 8 extends from the bottom part and a second height towards the top. The neck part 9 extends from the transitional part to the top 6 of the container. The first cavity 10 can be seen at the bottom of the container. The container is further provided with a lid 11.

Figure 2:
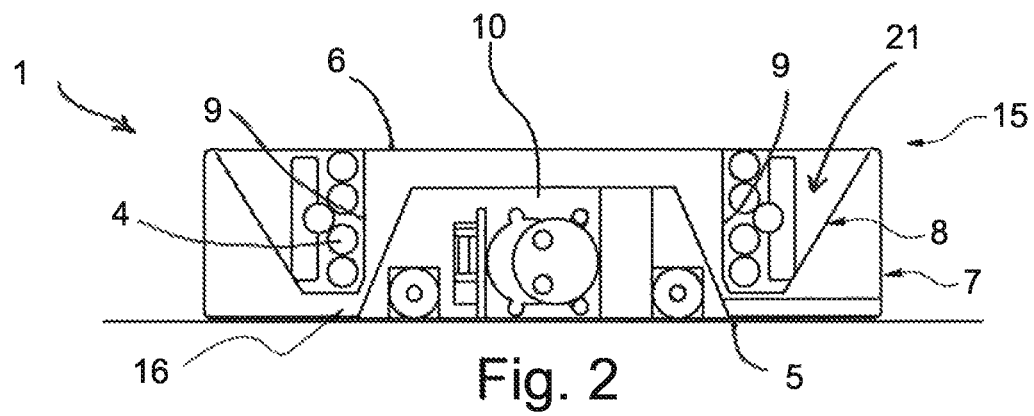
FIGS. 2 and 3 illustrate cross-sectional views of an embodiment of a container.
Figure 3:
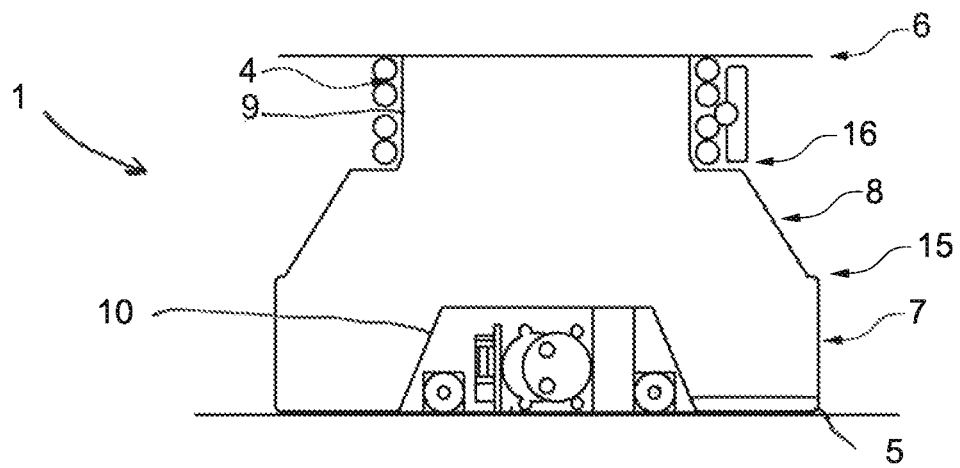

FIGS. 2 and 3 illustrate the same container as in FIG. 1—FIG. 2 illustrates a cross-sectional view of the container 1 in a collapsed configuration and FIG. 3 illustrates a cross-sectional view of the container 1 in an expanded configuration. In FIGS. 2 and 3, the container is illustrated as having the bottom part 7 connected to the transitional part 8 through a first hinge part 15 and the transitional part 8 connected to the neck part 9 through a second hinge part 16. These hinge parts allow the container to be collapsed, or folded onto itself, by folding the transitional part into the bottom part, and allow the neck part to stand up from the transitional part.

In the embodiment of FIGS. 2 and 3, the bottom 5 is wedge-shaped.

The neck part 9 of the container has an inner outline of a size allowing the first cavity 10 to be received within the neck part 9 in the collapsed configuration.

Figure 4:
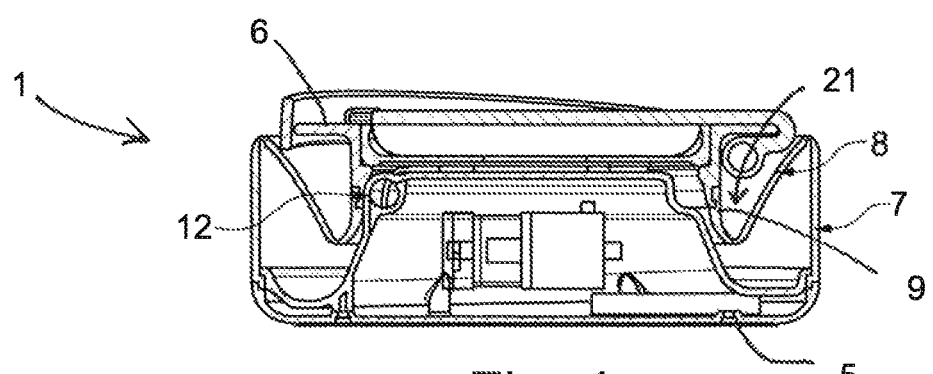
FIGS. 4 and 5 also illustrate cross-sectional views of an embodiment of a container. These figures illustrate a container with an inner tube extending from the bottom towards the outer surface of the container.
Figure 5:
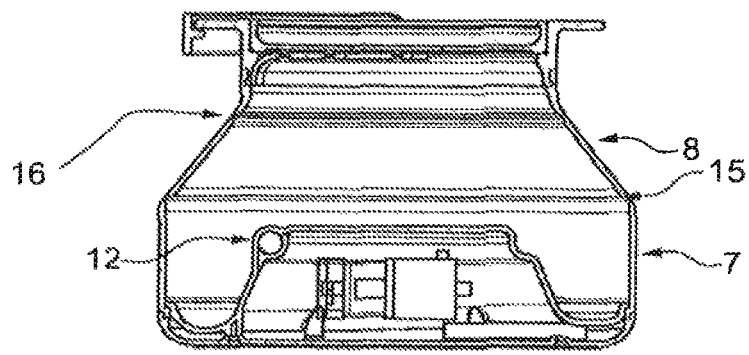

FIGS. 4 and 5 illustrate a cross-sectional view of an embodiment of the container. In FIG. 4, the container is illustrated in the collapsed configuration and in FIG. 5 in the expanded configuration. The bottom part 7 has the transitional part 8 folded into the third cavity. The illustrations show the second part of the inner tube 12. In FIG. 5, the first hinge part 15 between the bottom part 7 and the transitional part 8 is illustrated as well as the second hinge part 16 between the transitional part 8 and the neck part 9.

FIG. 6 illustrates another embodiment of the irrigation system. In FIG. 6, the container is shown in a cross-sectional view, allowing a view to the pump 13 and valves 14 in the first cavity 10. Furthermore, the second part 12 of the inner tube is shown inside the third cavity. Finally, the connection between the second part of the inner tube 12 and the outer tube 4 is shown, as well as the control unit 2 and the anal probe 3.

Figure 7:
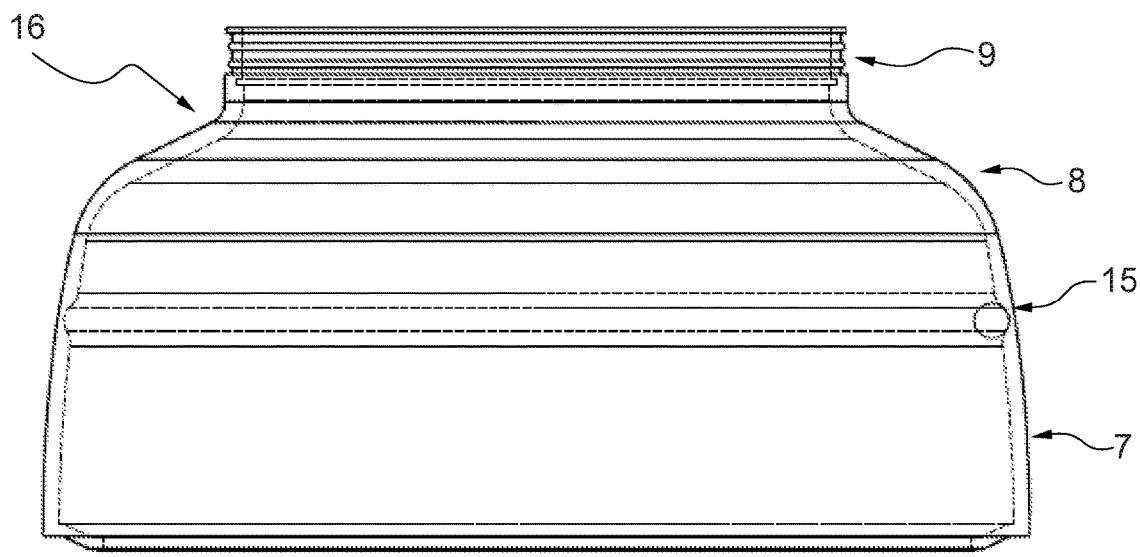
FIGS. 7 and 8 illustrate cross-sectional views of another embodiment of a container.
Figure 8:
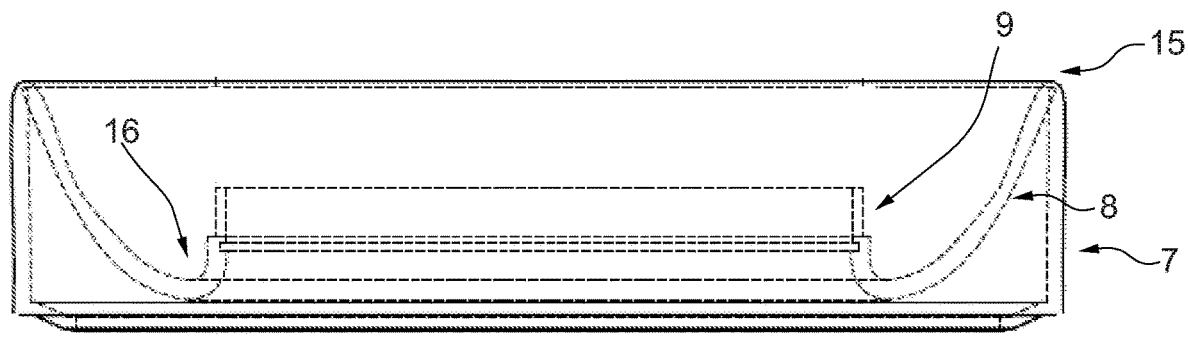

FIGS. 7 and 8 illustrate an embodiment of the container, FIG. 7 illustrates the container in an expanded configuration and FIG. 8 illustrates the container in a collapsed configuration. In the embodiment, the transitional part 8 is bi-stable in such a way that it bulges outward from the inner volume of the container in the expanded configuration and curves inward towards the inner volume of the container in the collapsed configuration. In this embodiment, there is no angle—or only a minor angle—in the connection between the bottom part 7 and the transitional part 8. The bottom part 7 and the transitional part 8 are connected through a first hinge part 15. There is an angle between the transitional part and the neck part. The transitional part 8 and the neck part are connected through a second hinge part 16.

The invention claimed is:

1. An irrigation system comprising:
   a container having a base and a base wall extending a first distance away from the base to a first hinge, a transition wall connected to the base wall and extending a second distance away from the base wall to a second hinge, and a neck portion connected to and extending from the transition wall to a top of the container, with the base, the base wall, the transition wall and the neck portion integrated to provide the container with a sidewall having an interior surface adapted to contain irrigation liquid;
   a section of tubing connected between a catheter and the interior surface of the container;
   wherein the container is collapsible from an expanded configuration to a collapsed configuration;
   wherein, when the container is in the collapsed configuration, the sidewall of the container is bent at the first hinge and bent at the second hinge such that a height of the container is equal to the first distance with the neck portion of the container located between the base and the first hinge;
   wherein, when the container is in the collapsed configuration, a trench is formed by the transition wall located at an outer boundary of the trench and the neck portion at an inner boundary of the trench with the second hinge located at a bottom of the trench, and a portion of the section of tubing is coiled around the neck portion and located in the trench between the neck portion and the transition wall.

2. The irrigation system of claim 1, wherein a first diameter of the container measured at the base wall is larger than a second diameter of the container measured at the neck portion.

3. The irrigation system of claim 1, further comprising a lid attachable to the neck portion.

4. The irrigation system of claim 1, wherein the section of tubing is exterior the container, and the irrigation system further comprising an inner tube inside of the container, where the inner tube extends from a pump located at the base of the container and is coupled with the section of tubing.

5. The irrigation system of claim 1, wherein the base wall of the container has a base wall thickness, and a thickness of the first hinge is less than the base wall thickness.

6. The irrigation system of claim 1, wherein the catheter is an anal irrigation catheter having an inflation channel communicating with an inflation balloon.

7. The irrigation system of claim 1, wherein the base is circular.

8. The irrigation system of claim 1, wherein a shape of the base is a polygonal shape in transverse cross-section.

9. The irrigation system of claim 1, wherein the interior surface of the sidewall defines a reservoir that is adapted to contain irrigation liquid, and the base forms an enclosed cavity that is separate from the reservoir.

10. The irrigation system of claim 1, wherein the container comprises two internal compartments including a reservoir that is adapted to contain irrigation liquid and an enclosed cavity containing an electrical pump.

11. The irrigation system of claim 1, wherein the portion of the section of tubing coiled around the neck portion of the container is located between the second hinge and the top of the container when the container is in the collapsed configuration.

12. The irrigation system of claim 1, wherein, when the container is in the collapsed configuration, the top of the container is located between the base and the first hinge.

13. The irrigation system of claim 1, wherein the container comprises a reservoir that is adapted to contain irrigation liquid and the trench forms an external dry compartment located radially outside of the exterior surface of the neck portion, with the section of tubing stored in the external dry compartment.

14. The irrigation system of claim 1, wherein the interior surface of the sidewall defines a reservoir that is adapted to contain irrigation liquid, and the base of the container forms an enclosed cavity that is separate from the reservoir, and the enclosed cavity contains a weight provided by a pump and valves, and the weight in the enclosed cavity allows the container to be popped open from the collapsed configuration to the expanded configuration.

15. The irrigation system of claim 1, wherein the top of the container has a radially extending lid that covers a top opening of the trench when the container is in the collapsed configuration.

* * * * *